(12) United States Patent
Strobel et al.

(10) Patent No.: US 6,926,684 B1
(45) Date of Patent: Aug. 9, 2005

(54) ORTHOPEDIC SPLINT

(75) Inventors: Michael Strobel, Mitterfels (DE); Jürgen Eichhorn, Mitterfels (DE); Karl Hausladen, Strubing (DE)

(73) Assignee: Medi Bayreuth Weihermuller und Voigtmann GMGH & Co. KG, Bayreuth (DE)

(*) Notice: Subject to any disclaimer, the term of this patent is extended or adjusted under 35 U.S.C. 154(b) by 0 days.

(21) Appl. No.: 09/171,732

(22) Filed: Oct. 8, 1998

Related U.S. Application Data

(63) Continuation of application No. PCT/DE98/00328, filed on Feb. 6, 1998.

(30) Foreign Application Priority Data

Feb. 8, 1997 (DE) ............................ 297 02 186 U

(51) Int. Cl.$^7$ ................................................. A61F 5/00

(52) U.S. Cl. ............................................. 602/5; 602/26

(58) Field of Search ............................... 128/846, 882, 128/877, 878, 879; 602/23, 26, 27

(56) References Cited

U.S. PATENT DOCUMENTS

| | | | | |
|---|---|---|---|---|
| 4,299,211 A | | 11/1981 | Doynow | 128/89 R |
| 4,423,720 A | * | 1/1984 | Meier | 128/80 |
| 4,708,130 A | | 11/1987 | Grudem | 128/78 |
| 4,794,917 A | | 1/1989 | O'Leary | 128/87 B |
| 4,852,556 A | | 8/1989 | Groiso | 128/87 R |
| 4,886,053 A | * | 12/1989 | Neal | 128/80 C |
| 4,953,543 A | * | 9/1990 | Grim | 128/80 C |
| 4,996,979 A | * | 3/1991 | Grim | 128/878 |
| 5,058,575 A | | 10/1991 | Anderson | 128/87 R |
| 5,069,229 A | * | 12/1991 | Kurth | 128/882 |
| 5,282,483 A | * | 2/1994 | Wang | 128/882 |
| 5,571,206 A | * | 11/1996 | Varn | 623/27 |
| 5,626,150 A | | 5/1997 | Johnson et al. | 128/870 |

\* cited by examiner

*Primary Examiner*—Michael A. Brown
(74) *Attorney, Agent, or Firm*—Thomas R. Vigil; Welsh & Katz, Ltd.

(57) ABSTRACT

The orthopedic splint (1) for maintaining the knee in a rest position, especially after surgery on the posterior cruciate ligament, comprises a covering section (2, 3, 4) with stabilizing sticks (6) as well as strips (7) to fasten the covering section (2, 3, 4) which is wrapped around the leg and wherein the covering section (2, 3, 4) has a padding for the calf in the corresponding area.

5 Claims, 4 Drawing Sheets

US 6,926,684 B1

ORTHOPEDIC SPLINT

CROSS REFERENCE TO RELATED APPLICATIONS

This is a continuing application of International Application PCT/DE98/00328, with an international filing date of Feb. 6, 1998.

BACKGROUND OF THE INVENTION

1. Field of the Invention

The invention relates to an orthopedic splint for maintaining the knee in a rest position, specially after surgery on the posterior cruciate ligament.

2. Description of the Prior Art

An orthopedic splint for maintaining the knee in a rest position comprising a covering section with stabilizing sticks arranged in pockets as well as hook and loop strips sold under the trademark VELCRO to fasten the covering section which is wrapped around the leg is known under the product name Medicom Classic for example. The covering section has wings fastened on it by means of hook and loop strips sold under the trademark VELCRO thanks to which the splint may be adapted to different leg sizes. This splint is used for injuries of the anterior cruciate ligament, the meniscus and the like. When the knee is normally stretched, the posterior cruciate ligament is tense. When the patient is lying, the dead weight of the leg is pulling the calf into the so-called posterior drawer and increases thus the tension on the posterior cruciate ligament. The strain thus exerted onto the posterior cruciate ligament, specially after reconstructive surgery, should be avoided in order to accelerate the healing process and to prevent the ligament from lazing.

SUMMARY OF THE INVENTION

An object of the present invention is therefor to provide an orthopedic splint for maintaining the knee in a rest position, by means of which the posterior cruciate ligament is relieved.

According to the invention, an orthopedic splint is provided comprising a covering section with stabilizing sticks as well as strips to fasten the covering section which is wrapped around the leg, wherein the covering section has a padding for the calf in the corresponding area. The padding for the calf is preferably sticking out of the splint in direction of the Achilles tendon and is provided on its lower part with an incision where it encompasses the Achilles tendon on both sides.

According to a preferred embodiment of the invention, the padding for the calf is consisting or a roamed body and is reinforced on the side turned away from the leg with a plastic brace, whereas the foamed body has a radius enabling it to snug the calf. The padding for the calf is fastened on the inner side of the covering section by means of a Velcro® fastener.

BRIEF DESCRIPTION OF THE DRAWINGS

The invention is described with more details with the help of the following drawings.

DESCRIPTION OF THE PREFERRED EMBODIMENT(S)

Figure 1:
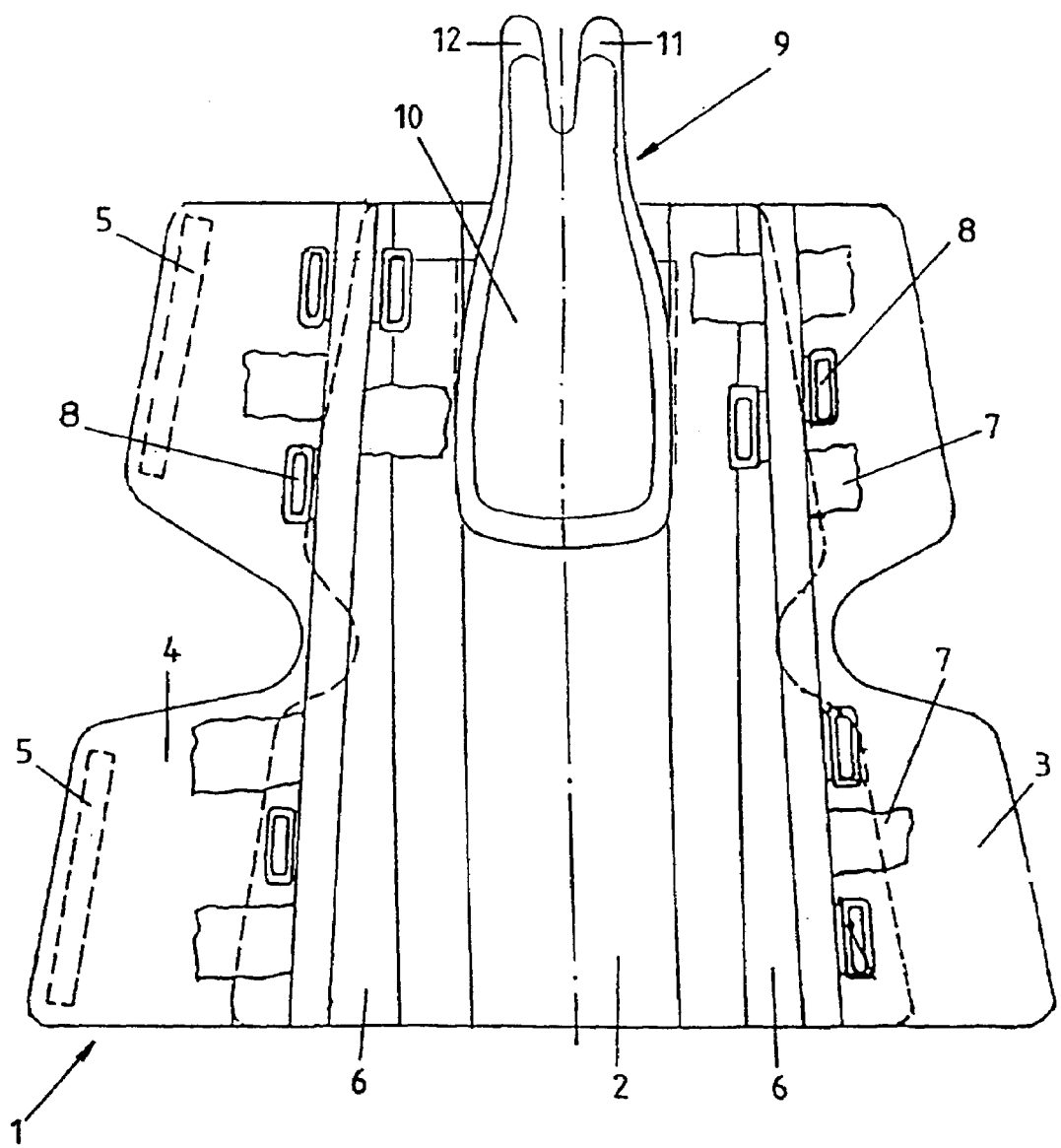
FIG. 1 shows a top view of an orthopedic splint with a padding for the knee in an open position.

The orthopedic splint 1 for maintaining the knee in a rest position according to Fig. ® The central part 2 and the lateral parts 3, 4 are removably connected for example by means of Velcro® fasteners so that they may be adapted to different leg sizes or situations. Stabilizing sticks 6 are arranged on the sides, that is in the areas being located at the side of the knee when the splint is applied. The sticks are preferably removably placed in pockets. The covering section is provided on its outer side with a Velcro® fleece onto which Velcro® strips 5 arranged on the outer side of lateral part 4 may be meshed. Radial Velcro® strips 7 fastened to the inner side of the covering section are responsible for the firm position of the splint on the leg. The radial Velcro® fasteners are guided outwardly through opposite eyes 8 and are then folded and may also be connected to the Velcro® fleece. The lower end of the covering section is provided with a padding 9 for the calf, the padding having an upper bulging section 10 which is tapered downwards and which ends in two extremities 11, 12 separated by a split. The padding 9 for the calf is sticking out of the lower part of the covering section.

Figure 2:
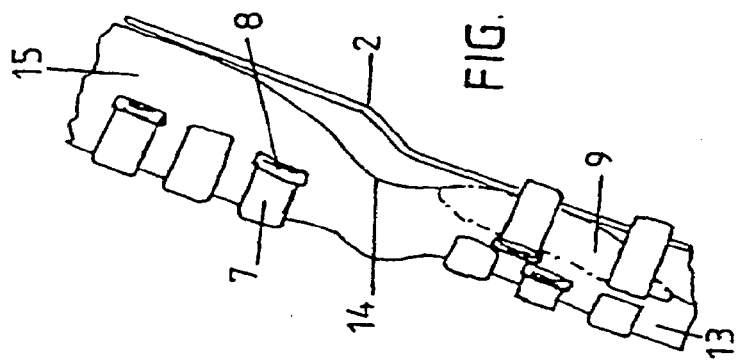
FIG. 2 is a schematic diagram of the splint shown in FIG. 1 applied to a knee.

FIG. 2 shows in a schematic diagram how the splint 1 is applied to the leg. A leg with thigh 15, knee 14 and calf 13 is shown. The splint is tightly wrapped around the leg by means of Velcro® strips guided through eves 8. The upper anterior Velcro® strips are thereby pushing the thigh backwards, the lower, posterior Velcro® strips are supporting the padding for the calf. The padding 9 for the calf, which is connected to the central part 2 of the covering section by means of a Velcro® fastener, is pushing onto the calf and exerts a forward directed force onto calf 13. It thus prevents the calf from being urged, in the area of the knee, into the so-called posterior drawer, since this would result in a lax ingrowth of the posterior cruciate ligament after surgery. It may also be seen that the padding for the calf is extending into the area of the Achilles tendon, which it supports laterally with its extremities 11, 12.

Figure 3:
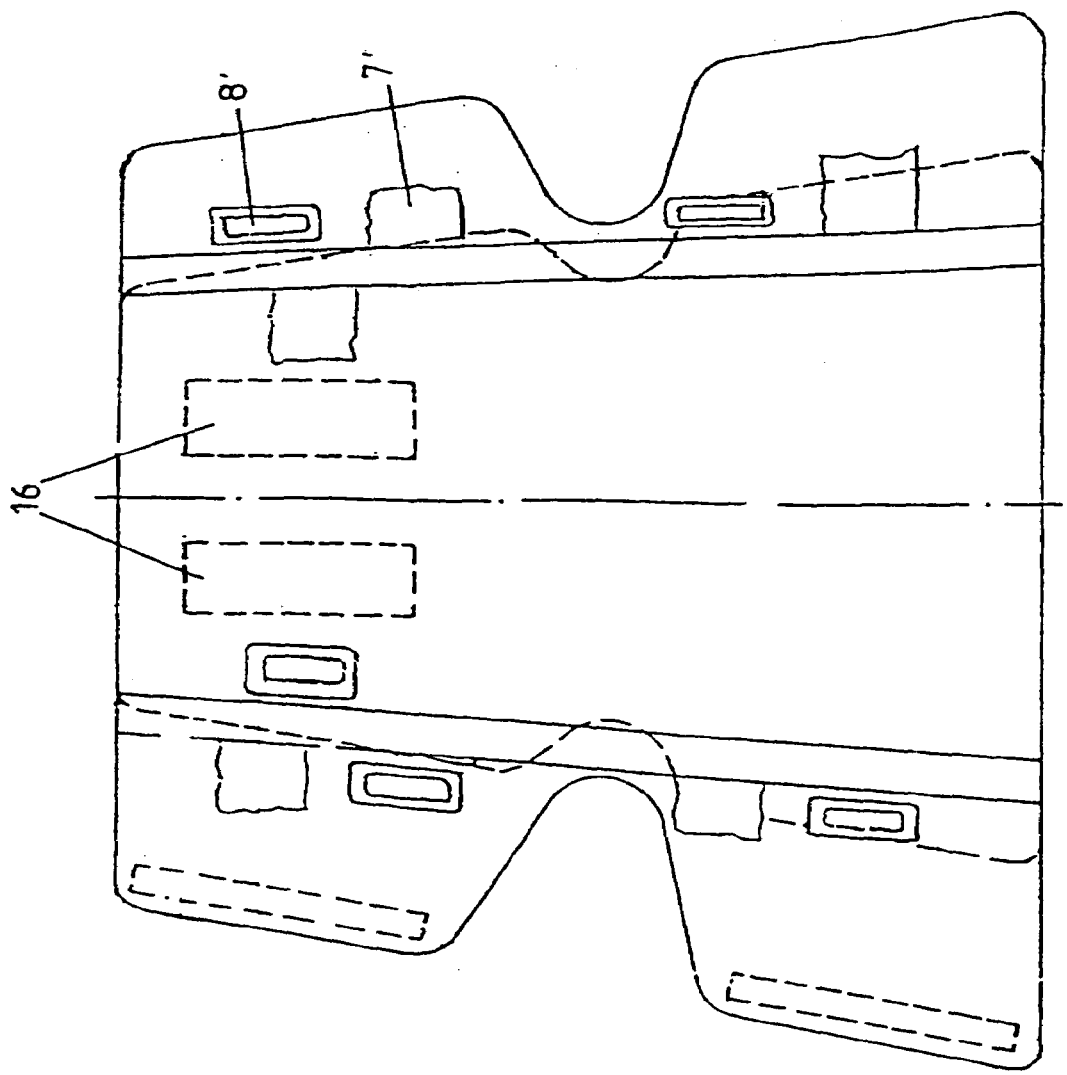
FIG. 3 shows an open splint slightly amended with respect to FIG. 1 without padding for the calf.
Figure 4:
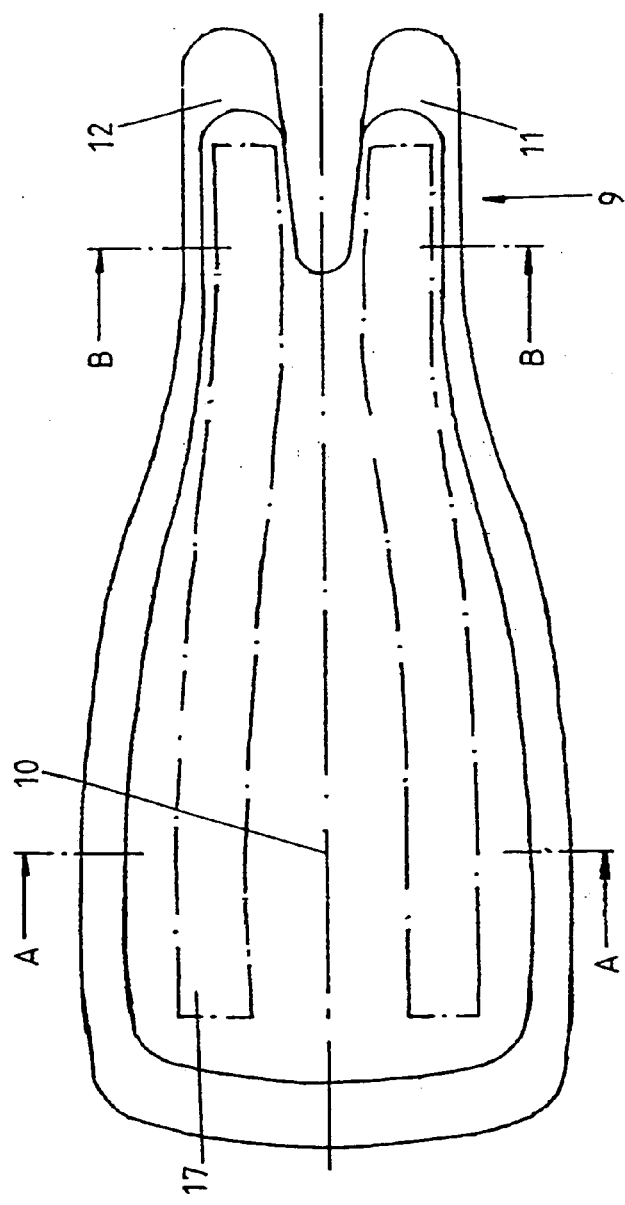
FIG. 4 is a top view of a padding for the calf.
Figure 5:
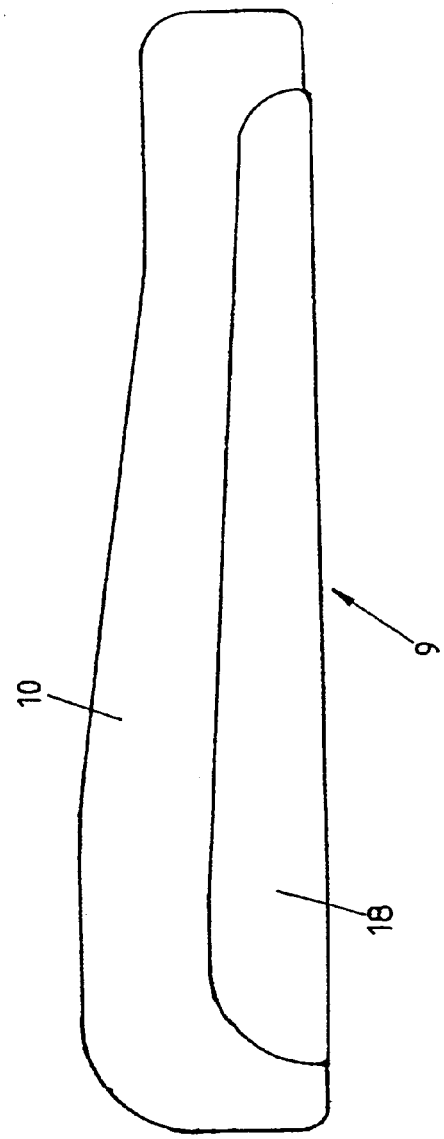
FIG. 5 is a lateral view of the padding shown in FIG. 4.
Figure 6:
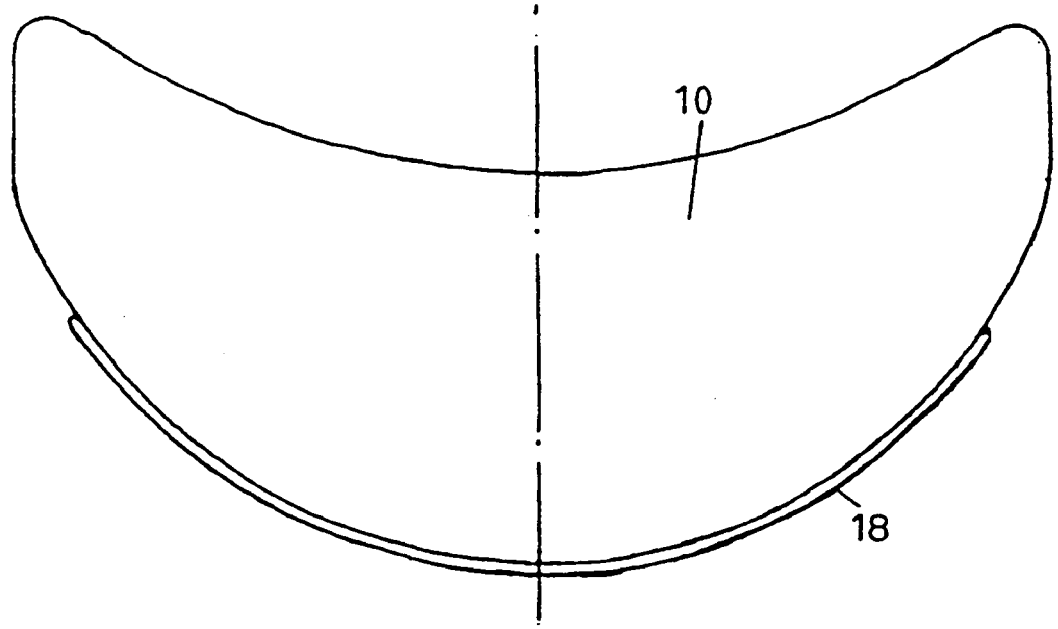
FIG. 6 is a sectional view taken along the line A—A of FIG. 4.
Figure 7:
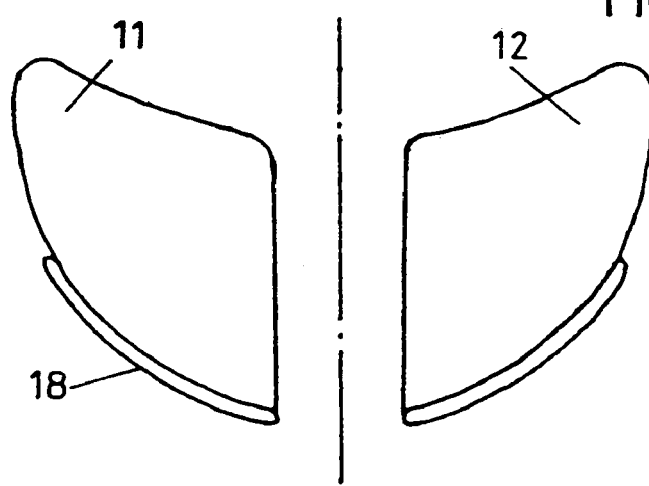
FIG. 7 is a section view taken along the line B—B of FIG. 4.

FIG. 3 is showing a smaller, slightly amended embodiment of the splint of FIG. 1, which has less Velcro® strips 7' and less eyes 8'. The padding for the knee is not inserted and the fleece strips 16, which may be meshed with the Velcro® strips of the padding for the calf, may be seen. Thanks to the Velcro® fastener between the padding for the knee and the covering section the splint may be individually adjusted to the leg.

The padding 9 for the calf according to FIGS. 4–7 has a bulging upper section 10 that is tapered downwards and ends in two extremities 11 and 12 as already shown in FIG. 1. It comprises a foamed body snuggling the calf, whereas the inner side of the foamed body is sheathed with a material kind to the skin and whereas the outer side is supported by a plastic brace 18. The plastic brace is extending over the biggest part of the padding's 9 length, its extremities inclusive. The padding 9 for the calf has inside and outside a radial radius adjusted to the calf. The Velcro® strips 17 which are arranged on the outer side of plastic brace 16 and which may be meshed with the fleece strips 16 of FIG. 3 are hinted at in FIG. 4.

We claim:

1. An orthopedic splint for maintaining the knee in a rest position, especially after surgery on the posterior cruciate ligament, said splint comprising a covering section with stabilizing sticks as well as tie strips which are constructed and arranged for fastening the covering section around the leg above and below the knee with the covering section positioned behind the leg and knee, wherein upper, anterior tie strips push the thigh backwards and lower posterior tie strips support a padding for the calf connected to a central part of the covering section, wherein said padding for the calf pushes onto the calf and exerts a forward directed force onto the calf and wherein the said padding for said calf comprises a foamed body which is reinforced, on the side of the padding away from the leg, with a plastic brace, and the foamed body has a radius enabling it to fit snugly about the calf.

2. Orthopedic splint of claim 1 for maintaining the knee in a rest position, especially after surgery on the posterior cruciate ligament, wherein the padding for the calf (9) protrudes out of the splint (1) toward the Achilles tendon.

3. Orthopedic splint according to claim 2, wherein the padding for the calf (9) only has a bifurcated lower end for encompassing the Achilles tendon on both sides.

4. Orthopedic splint according to claim 1, wherein the padding for the calf (9) is fastened on the inner side of the covering section by hook and loop fastening means.

5. Orthopedic splint according to claim 1, characterized in that the covering section comprises component parts (2, 3, 4) which may be connected in different positions.

* * * * *